United States Patent
Ong et al.

(10) Patent No.: US 12,411,009 B2
(45) Date of Patent: *Sep. 9, 2025

(54) TREMOR STABILIZATION APPARATUS AND METHODS

(71) Applicant: GyroGear Limited, London (GB)

(72) Inventors: Joon Faii Ong, London (GB);
Benjamin Gan, London (GB);
Benjamin Koh, Savannah, GA (US);
Xavier Laguarta Soler, London (GB);
Winston Choong Ngan Lou, London (GB); Paul de Panisse, London (GB);
Youssef Ibrahim, London (GB); Justas Medeisis, Vilnius (LT); Tiarvando, London (GB)

(73) Assignee: GyroGear Limited, Hertfordshire (GB)

( * ) Notice: Subject to any disclaimer, the term of this patent is extended or adjusted under 35 U.S.C. 154(b) by 16 days.

This patent is subject to a terminal disclaimer.

(21) Appl. No.: 17/388,738

(22) Filed: Jul. 29, 2021

(65) Prior Publication Data
US 2021/0356271 A1 Nov. 18, 2021

Related U.S. Application Data

(63) Continuation of application No. 15/539,089, filed as application No. PCT/GB2015/054128 on Dec. 22, 2015, now Pat. No. 11,079,225.

(30) Foreign Application Priority Data

Dec. 22, 2014 (GB) ...................................... 1422899

(51) Int. Cl.
*A61H 23/02* (2006.01)
*A61B 5/00* (2006.01)
(Continued)

(52) U.S. Cl.
CPC ............ *G01C 19/16* (2013.01); *A61F 5/0118* (2013.01); *A61H 23/02* (2013.01); *A61N 1/0484* (2013.01);
(Continued)

(58) Field of Classification Search
CPC ...... G01C 19/16; G01C 19/42; A63B 21/222; A63B 21/4019; A63B 21/00069;
(Continued)

(56) References Cited

U.S. PATENT DOCUMENTS 2,547,968 A * 4/1951 Paulus ................. G05D 1/0808
74/5.6 D
2,809,526 A * 10/1957 Lundberg ............... G01C 19/38
74/5 R
(Continued)

FOREIGN PATENT DOCUMENTS

CN 2092456 U * 1/1992
CN 104127187 A 11/2014
(Continued)

OTHER PUBLICATIONS

Falcao D [online], Imperial Create Lab: Gyroglove, available at http://imperialcreatelab.com/gyroglove/, version dated Jun. 4, 2014.
(Continued)

*Primary Examiner* — Tu A Vo
(74) *Attorney, Agent, or Firm* — Greenberg Traurig, LLP; David J. Dykeman; Kristopher Reichlen (57) ABSTRACT

The present invention relates to improvements in or relating to tremor stabilisation apparatus and methods, in particular to gyroscopic devices for use in controlling tremors of parts of the body and for reducing effects of tremors on the human body. The apparatus includes a wearable element and at least one gyroscopic device mounted or mountable to the wearable element, the gyroscopic device including a gyroscope
(Continued)

and a gyroscope housing. The at least one gyroscopic device may be mounted within the housing such that the gyroscope may precess with respect to the housing. The mount may include a hinge to which the gyroscope is mounted and a hinge plate or hinge mount to which the hinge is mounted for rotation with respect to the gyroscope housing, such as a turntable mounted to the gyroscope housing. The gyroscopic devices may include a control arrangement to control the precession of the gyroscope.

20 Claims, 8 Drawing Sheets (51) Int. Cl.

| | |
|---|---|
| A61B 5/01 | (2006.01) |
| A61B 5/021 | (2006.01) |
| A61B 5/024 | (2006.01) |
| A61B 5/11 | (2006.01) |
| A61F 5/01 | (2006.01) |
| A61N 1/04 | (2006.01) |
| A63B 21/00 | (2006.01) |
| A63B 21/22 | (2006.01) |
| A63B 23/16 | (2006.01) |
| A63B 24/00 | (2006.01) |
| F16F 7/10 | (2006.01) |
| G01C 19/16 | (2006.01) |
| G01C 19/42 | (2006.01) |
| A61B 5/0531 | (2021.01) |
| A61N 1/36 | (2006.01) |
| A63B 23/025 | (2006.01) |
| A63B 23/04 | (2006.01) |
| A63B 23/12 | (2006.01) |
| A63B 71/00 | (2006.01) |
| A63B 71/06 | (2006.01) |

(52) U.S. Cl.
CPC .. *A63B 21/00069* (2013.01); *A63B 21/00192* (2013.01); *A63B 21/222* (2015.10); *A63B 21/4019* (2015.10); *A63B 23/16* (2013.01); *A63B 24/0062* (2013.01); *A63B 24/0087* (2013.01); *F16F 7/1005* (2013.01); *G01C 19/42* (2013.01); *A61B 5/01* (2013.01); *A61B 5/021* (2013.01); *A61B 5/02438* (2013.01); *A61B 5/0531* (2013.01); *A61B 5/1101* (2013.01); *A61B 5/1117* (2013.01); *A61B 5/4266* (2013.01); *A61B 5/4809* (2013.01); *A61B 5/6804* (2013.01); *A61B 5/6806* (2013.01); *A61B 5/6824* (2013.01); *A61B 2562/0219* (2013.01); *A61F 2005/0155* (2013.01); *A61H 2201/0207* (2013.01); *A61H 2201/0271* (2013.01); *A61H 2201/1215* (2013.01); *A61H 2201/1604* (2013.01); *A61H 2201/1635* (2013.01); *A61H 2201/164* (2013.01); *A61H 2201/165* (2013.01); *A61H 2201/1659* (2013.01); *A61H 2201/5012* (2013.01); *A61H 2201/5084* (2013.01); *A61H 2201/5097* (2013.01); *A61H 2205/065* (2013.01); *A61N 1/36067* (2013.01); *A63B 21/4001* (2015.10); *A63B 21/4021* (2015.10); *A63B 23/025* (2013.01); *A63B 23/04* (2013.01); *A63B 23/12* (2013.01); *A63B 2024/0068* (2013.01); *A63B 2024/0093* (2013.01); *A63B 2071/0072* (2013.01); *A63B 2071/0655* (2013.01); *A63B 2209/08* (2013.01); *A63B 2209/10* (2013.01); *A63B 2220/13* (2013.01); *A63B 2220/30* (2013.01); *A63B 2220/40* (2013.01); *A63B 2220/803* (2013.01); *A63B 2225/09* (2013.01); *A63B 2225/20* (2013.01); *A63B 2225/50* (2013.01)

(58) Field of Classification Search
CPC .............. A63B 21/00192; A63B 23/16; A63B 24/0062; A63B 24/0087; A63B 21/4001; A63B 21/4021; A63B 23/025; A63B 23/04; A63B 23/12; A63B 2024/0068; A63B 2024/0093; A63B 2071/0072; A63B 2071/0655; A63B 2209/08; A63B 2209/10; A63B 2220/13; A63B 2220/30; A63B 2220/40; A63B 2220/803; A63B 2225/09; A63B 2225/20; A63B 2225/50; A61F 5/0118; A61F 2005/0155; A61H 23/02; A61H 2201/0207; A61H 2201/0271; A61H 2201/1215; A61H 2201/1604; A61H 2201/1635; A61H 2201/164; A61H 2201/165; A61H 2201/1659; A61H 2201/5012; A61H 2201/5084; A61H 2201/5097; A61H 2205/065; A61N 1/0484; A61N 1/36067; F16F 7/1005; A61B 5/01; A61B 5/021; A61B 5/02438; A61B 5/0531; A61B 5/1101; A61B 5/1117; A61B 5/4266; A61B 5/4809; A61B 5/6804; A61B 5/6806; A61B 5/6824; A61B 2562/0219
See application file for complete search history.

(56) References Cited

U.S. PATENT DOCUMENTS

| | | | | |
|---|---|---|---|---|
| 2,811,042 | A * | 10/1957 | Kenyon | G01C 21/18 74/5.22 |
| 3,006,197 | A * | 10/1961 | Kenyon | G02B 27/644 359/557 |
| 3,413,973 | A * | 12/1968 | Teranishi | A61H 23/0263 601/16 |
| 4,020,491 | A | 4/1977 | Bieser et al. | |
| 4,355,541 | A | 10/1982 | Okubo | |
| 4,696,196 | A * | 9/1987 | Vucevic | H01Q 1/18 74/5.22 |
| 5,058,571 | A | 10/1991 | Hall | |
| 5,396,815 | A | 3/1995 | Polites | |
| 11,079,225 | B2 * | 8/2021 | Ong | A63B 24/0062 |
| 2003/0006357 | A1 * | 1/2003 | Kaiser | A61H 23/02 248/550 |
| 2003/0025721 | A1 * | 2/2003 | Clapper | G06F 3/0354 715/700 |
| 2003/0236475 | A1 * | 12/2003 | Kalvert | A61F 5/0118 601/40 |
| 2008/0034383 | A1 | 2/2008 | Harwin et al. | |
| 2008/0242508 | A1 | 10/2008 | Smith | |
| 2009/0326422 | A1 * | 12/2009 | Hoffman | A61F 5/013 601/5 |
| 2010/0231069 | A1 | 9/2010 | Liao et al. | |
| 2013/0040783 | A1 * | 2/2013 | Duda | A63B 21/225 482/9 |
| 2013/0123666 | A1 | 5/2013 | Giuffrida et al. | |
| 2013/0210577 | A1 * | 8/2013 | Ceoldo | A63B 21/00196 482/1 |
| 2013/0237377 | A1 | 9/2013 | Wilkinson et al. | |
| 2014/0055271 | A1 * | 2/2014 | Chowdhary | G08B 21/18 340/600 |
| 2015/0272807 | A1 | 10/2015 | Gupta et al. | |
| 2018/0266820 | A1 | 9/2018 | Ong et al. | |
| 2018/0289309 | A1 | 10/2018 | Chen et al. | |

(56) References Cited

U.S. PATENT DOCUMENTS

FOREIGN PATENT DOCUMENTS

| | | | | | |
|---|---|---|---|---|---|
| DE | 10251275 | A1 * | 5/2004 | ......... | A63B 21/0004 |
| GB | 810440 | A | 3/1959 | | |
| WO | 2001080710 | A2 | 11/2001 | | |
| WO | 2013136287 | A1 | 9/2013 | | |
| WO | 2014053041 | A1 | 4/2014 | | |

OTHER PUBLICATIONS founder.org [online], GyroGlove, available at https://founder.org/gyroglove, version dated Mar. 29, 2014.
C Johnson, Parkinson Tremor Elimination with a Gyroscope and Physics, mb-soft.com/public3/parkin77.html, dated Feb. 1, 2013, XP055484932.
Johnson, C [online], Parkinson's Tremors Eliminated with Physics and a Gyroscope, available at http://mb-soft.com/public3/parkin77.html, version dated Apr. 2013.
Oxbridge Biotech [online], Roundtable: The Winner takes it all: Eva Diagnostics wins OBR's 2014 OneStart Competition, available at http://www.oxbridgebiotech.com/review/onestart/winner-takes-obr-onestart-competition-2014-final/, version dated May 23, 2014.
International Searching Authority, International Search Report and Written Opinion, PCT Patent Application Serial No. PCT/GB2015/054128, dated Jun. 8, 2016.
European Patent Office, European Examination Report, European Patent Application No. 15828831.6-1126 which is a national stage application of International Application Serial No. PCT/GB2015/054128 dated Oct. 23, 2018.
United Kingdom Intellectual Property Office (UKIPO), Patents Act 1977: Combined Search and Examination Report Under Sections 17 and 18(3), Great Britain Patent Application Serial No. GB1422899.3, dated Dec. 22, 2016. UK.

* cited by examiner

TREMOR STABILIZATION APPARATUS AND METHODS

RELATED APPLICATIONS

This application is a continuation application of U.S. application Ser. No. 15/539,089, filed Jun. 22, 2017, which is 35 U.S.C. 371 national stage application of PCT International Patent Application No. PCT/GB2015/054128, filed Dec. 22, 2015, which claims the benefit of and priority to GB Patent Application No. 1422899.3, filed Dec. 22, 2014. The contents of each of these applications are hereby incorporated by reference in their entirety into this disclosure.

FIELD OF THE INVENTION

The present invention relates to improvements in or relating to tremor stabilisation apparatus and methods, in particular to gyroscopic devices for use in controlling tremors of parts of the body, both physiological and pathological, especially the hands.

BACKGROUND OF THE DISCLOSURE

Involuntary muscle tremors occur in a range of neurological conditions, notably degenerative conditions such as Parkinson's disease.

Numerous proposals for mediating hand tremors using gyroscopes have been proposed. U.S. Pat. No. 5,058,571 describes an early proposal in which a battery-driven gyroscope is held against the back face of the hand by a strap. A gyroscope seeks to maintain the orientation of its spinning axis and resists any action that seeks to cause a change in that orientation. Thus, the theory of using a gyroscope is that the onset of a muscle tremor causes a movement in the hand but the gyroscope acts against that movement, substantially cancelling out the tremor.

However, as noted in U.S. Pat. No. 6,730,049, the device of U.S. Pat. No. 5,058,571, having a single gyroscope, is capable only of reducing involuntary movement in one planar direction. However, involuntary movements are rarely one-dimensional with respect to arm movement. U.S. Pat. No. 6,730,049 proposes a splint to bind the user's lower arm, wrist and hand, leaving just the thumb and fingers free. Thus, any involuntary movement within the bound area, irrespective of dimension, is transferred to the splint. A gyroscope is mounted to the splint in such a position that it counters this movement. In some embodiments, two gyroscopes are mounted to the splint with their rotational axes mounted orthogonally to one another. The device is claimed to be tuneable to a particular patient's tremor profile by adjustment of the location of the gyroscope along the length of the splint.

However, the skilled person will immediately appreciate that this device prevents all free movement within the lower arm other than of the fingers. Even movement of the thumb is considerably restricted, severely limiting the patient's range of activities, potentially exacerbating the practical consequences of the patient's condition rather than alleviating it.

Accordingly, there is a need for improved tremor stabilisation techniques.

SUMMARY OF THE DISCLOSURE

In its broadest sense, the present invention provides an apparatus for reducing effects of tremors on the human body. The apparatus comprises a wearable element and at least one gyroscopic device mounted or mountable to the wearable element, the gyroscopic device comprising a gyroscope and a gyroscope housing. The apparatus is characterised in that the at least one gyroscopic device is mounted within the housing by means of a mount which allows the gyroscope to precess with respect to the housing.

In one embodiment, the mount comprises a hinge to which the gyroscope is mounted and a hinge plate or hinge mount to which the hinge is mounted for rotation with respect to the gyroscope housing.

Preferably the hinge plate or hinge mount comprises a turntable mounted to the gyroscope housing.

Preferably, the or each gyroscopic device further comprises a control arrangement to control the precession of the gyroscope.

In certain embodiments, the control arrangement comprises a plurality of elastomeric dampers.

Additionally, or alternatively, the control arrangement comprises a magnetic control arrangement, preferably comprising at least one magnetic disc or annular magnet associated with the gyroscope.

Suitably, the control arrangement includes a motor, preferably a stepped motor, and drive arrangement associated with the turntable, preferably a direct drive arrangement, such as a gear assembly, or a belt drive arrangement.

In one embodiment, the apparatus comprises a plurality of gyroscopic devices. Preferably, the plurality of gyroscopic devices are distributed across a surface or surfaces of the wearable element.

Preferably, the gyroscope housing includes a switchable control circuit controlling the operation of the or each gyroscope. More preferably, the control circuit includes a switch mounted to the gyroscope housing.

Preferably, the apparatus further comprises a battery power supply, preferably a rechargeable battery power supply, more preferably, a rechargeable battery power supply system rechargeable by a near-field wireless or induction charging system.

Preferably, the gyroscopic devices are powered wirelessly and the apparatus further comprises a wireless power control circuit.

Preferably, the wearable element is a glove, sock, shoe, strap or headgear.

Preferably, the apparatus further comprises at least one of: an accelerometer; one or more sensors, including fall sensors, sleep sensors, body metrics sensors such as blood pressure, pulse, temperature, skin conductivity and sweat sensors.

Optionally, the apparatus further includes a voice-recognition control system.

Preferably, the or each gyroscopic device includes a gyroscope disc having a plurality of radially directed lines of weakness formed therein.

Preferably, each gyroscopic device has a gyroscope disc formed with a plurality of radial fingers. More preferably, a radial length of each finger is adjustable.

Preferably, each gyroscopic device has a gyroscope disc driven by a motor and wherein the apparatus further comprises adjustment means for adjusting or modulating a current through the motor or voltage applied to the motor.

Preferably, the apparatus further comprises a global positioning system and tracking functionality.

Preferably, the apparatus further comprises wireless networking functionality linkable to external computer-based systems, such as computers, including remote computers, and mobile devices such as smartphones, laptops and tablet devices.

Preferably, the apparatus further comprises a heat-management arrangement, to remove heat generated by the gyroscopic devices.

In some embodiments, the heat management arrangement comprises the use of a heat-conductive casing to the gyroscopic devices. The heat management arrangement may also comprise a heat sink, optionally a heat sink forming a part of a casing to the gyroscopic devices. In preferred embodiments, heat recovered from the gyroscopic device is channelled to the wearable element to provide a heating function.

BRIEF DESCRIPTION OF THE DRAWINGS

The above and other aspects of the present invention will now be described in further detail, by way of example only, with reference to the accompanying figures, in which.

DETAILED DESCRIPTION

A gyroscope is a device having a rotatable disc which is freely rotatable about an axis. As the disc rotates, the gyroscope will resist the action of an applied couple and tends to maintain a fixed orientation. If the gyroscope is rotationally displaced, angular momentum is conserved through nutation of the device about an axis which is mutually perpendicular to the axis of disc rotation and the axis through which the device is displaced.

A gyroscope will exert a gyroscopic moment which is proportional in magnitude to the moment of inertia of the disc, the angular velocity of the disc and the angular velocity of nutation. The direction vector of the gyroscopic moment is proportional to the vector cross product of the angular velocity of the disc and the angular velocity of the nutation of the device.

The apparatus of the present invention includes a plurality of gyroscopic devices spaced about the part of the body to which the apparatus is applied. The plurality of gyroscopic devices together apply a cumulative net gyroscopic moment to the body when the state of equilibrium of the body is perturbed, such as during a tremor or rotational displacement, but allows for the use of smaller gyroscopes, thereby spreading the mass of the gyroscopes across the body part making the device easier to wear and also reducing the bulk of the apparatus, thereby hindering dexterity and movement to a lesser degree than with known devices with larger gyroscopes.

Figure 1:
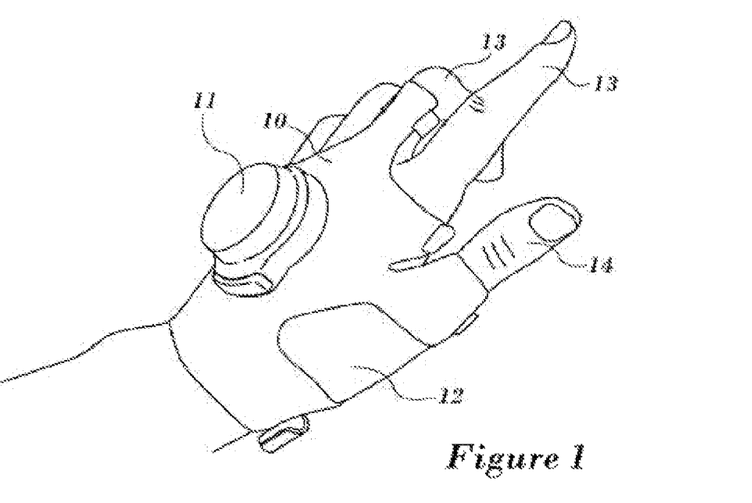
FIG. 1 shows an embodiment of an apparatus in accordance with the present invention in attached to a hand.

FIG. 1 shows an embodiment of an apparatus in accordance with the present invention in the form of a glove 10 having a gyroscopic device 11 mounted thereto on the back of a hand 12. In the embodiment shown, glove 10 is of the open or fingerless type to allow free-movement of the fingers 13 and thumb 14. Preferably, the glove is formed as a fabric support for the gyroscopic device, attachable to the wrist, fingers and thumb of the wearer by means of straps, suitably straps using a hook and loop-type adjustable securing arrangement. The fabric is preferably of a soft, comfortable material that it can be worn comfortably for extended periods of time. In preferred embodiments, the fabric is of the type described in WO 2014/127291 in which van der Waals forces are developed between a soft silicone fabric surface and a wearer's skin, to retain the fabric in place.

Figure 2:
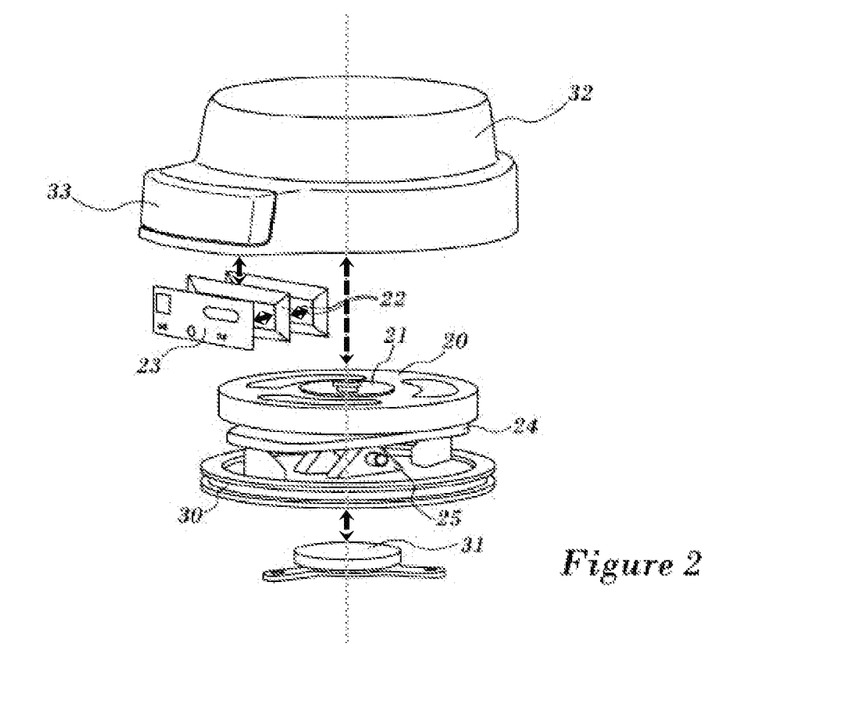
FIG. 2 is an exploded view of the gyroscope and gyroscope housing of the embodiment of FIG. 1.

FIG. 2 is an exploded perspective of a preferred embodiment of a gyroscopic device. The gyroscope includes a rotatable disc 20, suitably a metal disc, such as a brass disc, driven by a brushless DC motor 21. In the embodiment shown, the gyroscope is driven by a small DC power supply in the form of batteries 22 controlled by control circuit 23. In alternative arrangements, the power supply and control circuit are remote from the gyroscope device.

Motor 21 of the gyroscope is mounted to a gyroscope table 24 which is, in turn, mounted to a precession hinge 25, mounted to a hinge plate 30. Hinge plate 30 is mounted to a turntable 31 which is, in turn, fixedly secured to glove 10 of the apparatus. Thus, in use, the axis of the gyroscope is able to precess by virtue of the two-axis anchoring provided by the combination of the precession hinge 25 and turntable 31.

Precession, and controlled precession of the gyroscope axis ensures that the resultant vector of resistance of the apparatus is always substantially in opposition to the tremor vector.

Elastomeric dampers are provided between hinge plate 30 and gyroscope table 24 to limit the precessional angle, being the angle between the axis of precessing gyroscope and an axis normal to the hinge plate 30.

In certain embodiments, magnets are incorporated to the or each gyroscope device, either in place of the elastomeric dampers or in addition, to further control the precession of the gyroscope. For example, one or more magnetic discs or rings or a toroidal magnet are disposed about the gyroscope disc 20, to control its precession. Alternative arrangements are equally suitable, such as springs and variable electromagnets. Additionally, orientation of the turntable can be controlled, for example by means of a stepping motor and gear arrangement, to provide further control over multiple axes of tremor with a single gyroscope.

A housing 32, attachable to the glove, encloses the gyroscope and, in the embodiment shown, provides an actuator, in the form of a switch 33, to turn the motor on and off.

Figure 3A:
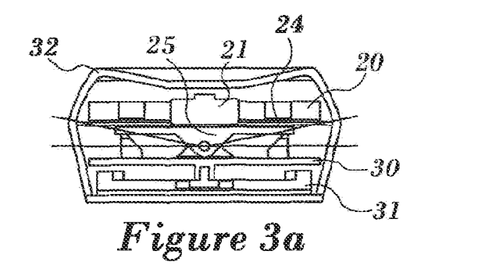
FIGS. 3A, 3B and 3C are cross-sectional views of the gyroscope and housing of the embodiment of FIG. 1.
Figure 3B:
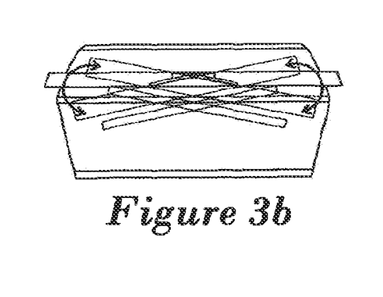
Figure 3C:
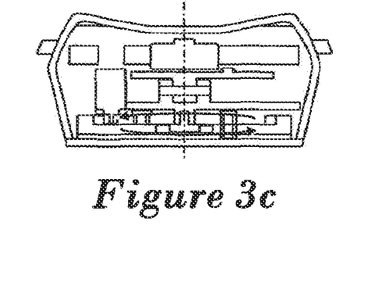

FIG. 3 shows the gyroscopic device in more detail in cross-section, in both a rest orientation (FIG. 3a) and in a precessing orientation (FIG. 3b). FIG. 3c shows the inclusion of a stepped motor gear assembly to provide additional control to the turntable and thus provides additional control of precession. Alternative control systems are equally suitable, such as other direct drive assemblies or belt drive assemblies.

Figure 4:
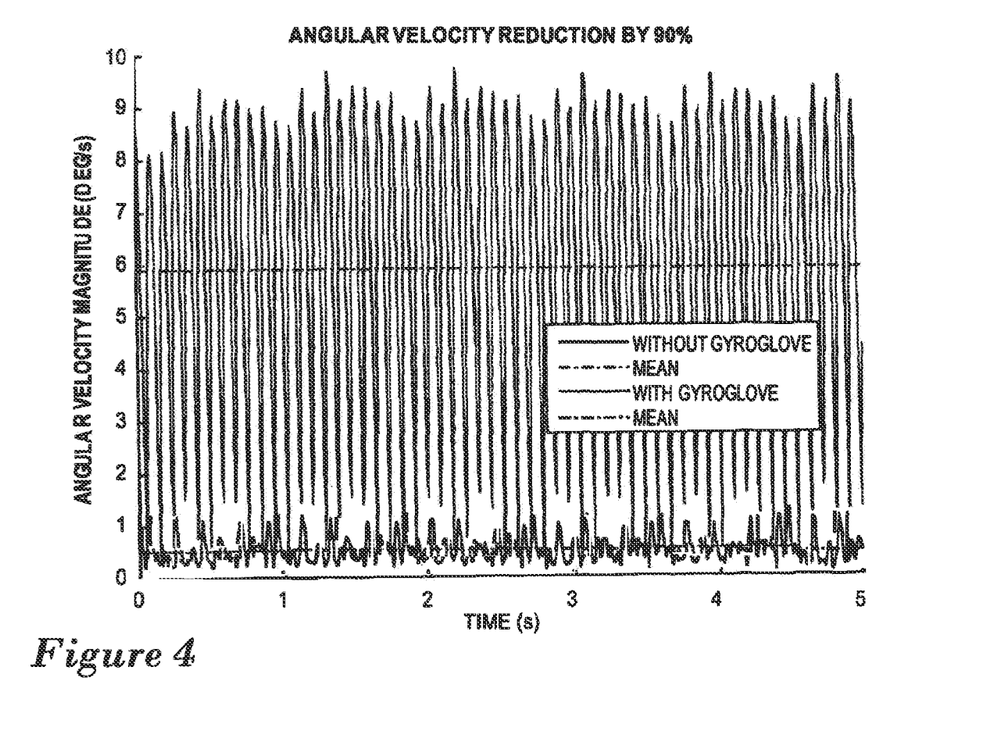
FIG. 4 is a graph illustrating the performance of the embodiment of FIG. 1.

FIG. 4 shows the results obtained with the apparatus of FIGS. 1 to 3. In the experiments, the apparatus was attached to a wooden artist's jointed hand which was attached to a support to which a motor having a mass attached eccentrically to the spindle of the motor to induce shaking of the hand. With the apparatus attached to the hand, but not operating, a mean angular velocity magnitude of about 6 degrees per second was seen, with an amplitude from about −5.5 to +3.5. In contrast, with the apparatus of the present invention operating, the mean angular velocity magnitude was reduced to about 0.5 degrees per second, with an amplitude of from about −0.3 to about +0.7. The same performance was viewed qualitatively in a 70 year old female patient diagnosed with Parkinson's Disease and exhibiting strong hand tremors.

In some embodiments, as will be described in further detail below, the gyroscope disc is integrated into the motor and acts as the motor, mounted with a permanent magnet acting as the housing.

Figures 5A, 5B, 5C:
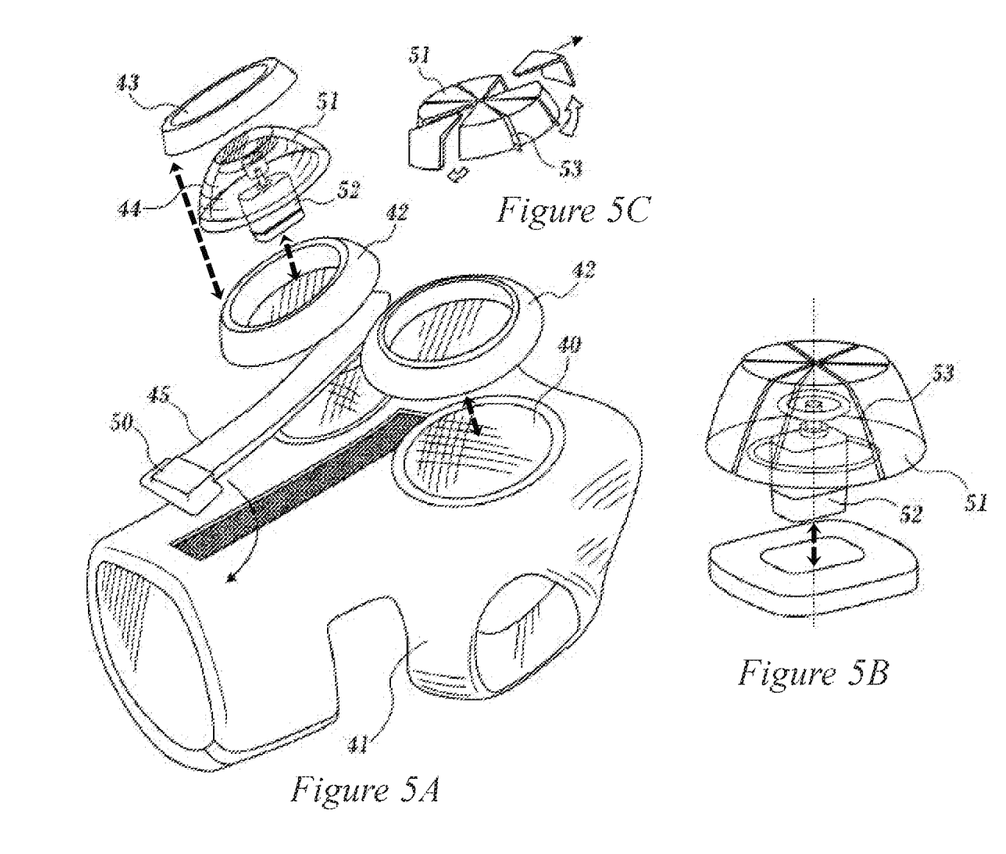
FIGS. 5A, 5B and 5C are perspective views of a further embodiment of an apparatus in accordance with the present invention in the form of a glove.

An alternative embodiment is illustrated in several views in FIGS. 5A, 5B and 5C. In this embodiment, a gyroscope mount 40 is formed within or attached to a glove element 41. Mount 40 includes a gyroscope-receiving cup 42 for each of the plurality of gyroscopes and an associated demountable cap 43 forming a gyroscope housing for a gyroscopic device 44. In the embodiment shown, mount 40 includes a stem 45 connecting the housing with a battery-housing 50. Cups 42 and stem 45 can be formed integrally with the glove or formed as a demountable unit, allowing for replacement as and when necessary and allowing for the use of a single mount arrangement with a range of glove sizes or, indeed, other forms of attachment to the human body, such as straps, socks, shoes and so on.

Gyroscopic device 44 includes a gyroscope disc 51 and motor 52.

Gyroscope-receiving cup 42 includes such electrical connections as are necessary for coupling the respective gyroscope to the battery supply 50, optionally by hard-wiring of the gyroscope, but preferably by means of electrical contacts or pads within the cup against which corresponding contacts or pads upon the gyroscope unit press and are held securely in place by demountable cap 43.

With the use of a mount 40 of the type described, providing a housing individually for each gyroscope, the individual gyroscopes can be selected to provide different torques from one another if desired, for example if tremors are more prevalent in one particular area or if tremors give rise to larger effects in certain areas of the body. As such, the apparatus of the present invention can be tuned to a particular patient's needs.

It will be appreciated that the gyroscopic devices need to be securely mounted to the glove or other wearable unit such that gyroscopic torque is transferred to the wearer's body rather than being absorbed by, for example, stretching or other movement of the glove. Suitable tensioning can be achieved by the use of elastic members, tensioned wires or similar arrangements; or by inclusion of such elements within the body of the wearable component.

It will be appreciated that miniature gyroscopes have a considerably smaller power requirement than large gyroscopes of the type used in the prior art devices described above. Even with the use of a plurality of small gyroscopes, the total power requirement of devices of the present invention is typically considerably less than that of the prior art. As such, small, lightweight and unobtrusive button cells can be used.

Alternatively, small rechargeable batteries can be used, suitably lithium ion or lithium ion polymer cells. In one arrangement, the rechargeable cells are rechargeable by means of a plug-in connector such as those that are well known in the field of electronic devices, for example, a connection attachable by means of a lead to a USB-powered connection, usually at 5 Volts (V). In alternative embodiments, the rechargeable batteries are rechargeable by means of an induction charging device. Such arrangements are well known in the field and will not be described in further detail.

In a further alternative embodiment, the gyroscopes used in the apparatus are powered directly by a wireless power transmission arrangement without the need for batteries. However, such an apparatus nevertheless preferably includes batteries to provide a backup power supply.

In certain embodiments, additional power supplementation is provided, such as through harnessing of light energy, electromagnetic radiation, thermal gradients and motion. Suitable arrangements include:

Photovoltaics cells harvesting light energy lining the device surface, optionally with a transparent scratch resistant protective layer protecting the cells underneath;

Thermoelectric generators exploiting thermal gradients established between body temperature and environment to generate electricity. Optionally, heat generated by motors can be used to establish thermal gradients in relation to a suitable cooling apparatus;

Piezoelectric transducers which convert mechanical strain into current or voltage lining areas of the glove prone to deformation;

Microfluidic energy harvesters generating electricity through conversion of kinetic energy in the form of vibration, shear and flow into electrical energy.

Power generation through motion capture is considered to be of particular interest, particularly embedded microfluidic energy harvesting REWOD-based vibration harvesting. A REWOD process works by generating electricity as a conductive droplet changes position or shape, and thereby its area and position of contact with two oppositely charged dielectric coated electrodes. One design incorporating multiple harvesters encompasses one or more of:

Conductive fluid droplets (e.g., Galinstan) between oscillating plates reclaiming energy from the vibrations of motors;

Flexible fluidic chambers incorporated into the palmar aspect of a glove (for example) with fluidic channels lined with associated electrodes running along the dorsal aspect of apparatus;

Piezoelectric transducers at palmar surface harnessing energy expended during grip;

Sliding electrodes harnessing material shear along the wrist joint by enabling conductive fluid droplets to shear along the electrodes.

Through harnessing ambient energy, it becomes possible for the apparatus to achieve autonomous power generation.

The apparatus may further include current or voltage modulation circuitry to allow variation of the speed of rotation of the gyroscope disc 20,51 to allow for additional adjustment and fine tuning of the gyroscopic torque. In the preferred embodiments including telecommunications modules, fine tuning of the device through current or voltage adjustment can be achieved remotely, for example, by means of a computer, such as a computer operated remotely by a clinician, or by means of a portable device, preferably a touch-screen device, for ease of use by the patient, such as a smartphone or tablet computer. This feature allows for the incorporation of additional functionality and monitoring into the application or program running on the device, such as the display of system information and health metrics; and to allow for user customisation and programming.

In certain embodiments, the housing for the gyroscope is sealed and the cavity filled with a gas at a density less than that of atmospheric air or the cavity is under vacuum, to reduce air resistance upon the rotating gyroscope, thereby reducing power draw and increasing efficiency and reliability.

Although illustrated thus far with one or two gyroscopes, the present invention provides apparatus with any number of gyroscopes, to take account, for example, of tremor on a plurality of axes.

As is shown in FIGS. 5A, 5B, 5C and 6, in preferred embodiments, the gyroscope disc 51 is advantageously formed with fracture lines 53 and/or fingers 54. Fracture lines 53 form lines of weakness in the disc structure such that, in the event of damage to the gyroscope causing damage to the disc, such as might follow a fall against a hard surface, the disc is encouraged to fracture in a controlled manner. This reduces the likelihood of disc fragments breaching the containment of the cap 43 or the entire housing, mounting and glove.

Additionally, the gyroscope may be constructed with a braking system, to provide rapid deceleration of the disc, both for use and safety reasons. Regenerative braking is preferred to supplement the power supply of the device.

Figure 6:
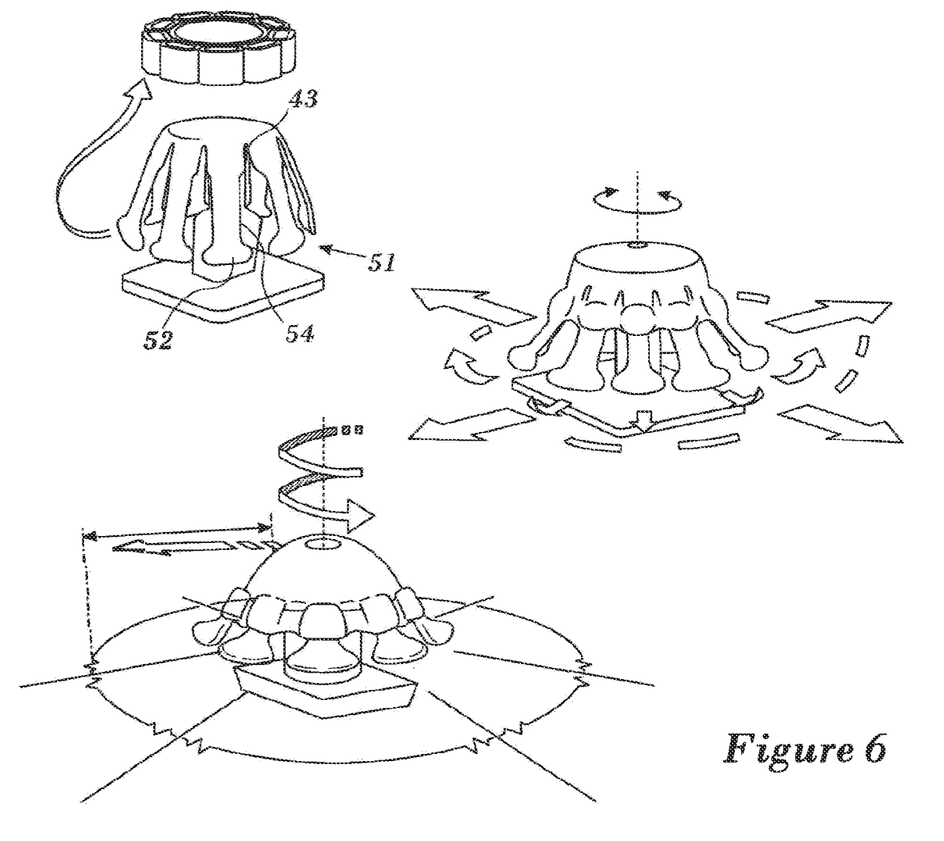
FIG. 6 shows, in several view, a further alternative gyroscope disc arrangement.

As shown in FIG. 6, formation of gyroscope disc 51 with a plurality of fingers 54, allows adjustment of the legs to adjust the radial dimensions of the disc 51, thereby adjusting the torque profile of the gyroscope. The radial extent of each leg 54 may be adjusted to increase the diameter of the disc as a whole or individual legs may be adjusted to give fine adjustment to the characteristics of the gyroscopic device. This method of adjusting the characteristics of a gyroscope forms a distinct and general aspect of the present invention.

In preferred embodiments, such as those shown in FIG. 6 and in FIG. 8A through FIG. 8D described below, the fingers have an additional elastic component that induces contraction to the rotational axis in the event of failure, thereby further reducing the risk of facture components breaching the housing. Suitably, the elastic component is formed by an elastic polymeric material or one or more springs.

Figure 7:
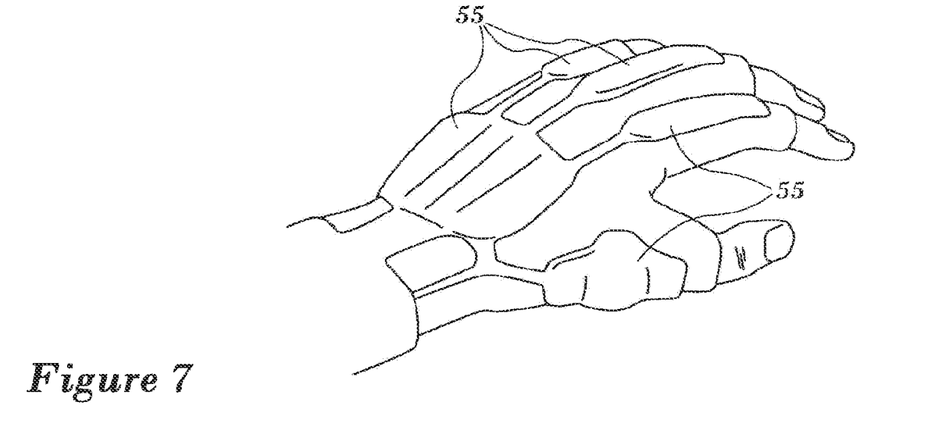
FIG. 7 is a perspective view of a yet further embodiment of an apparatus in accordance with the present invention in the form of a glove.
Figure 8A:
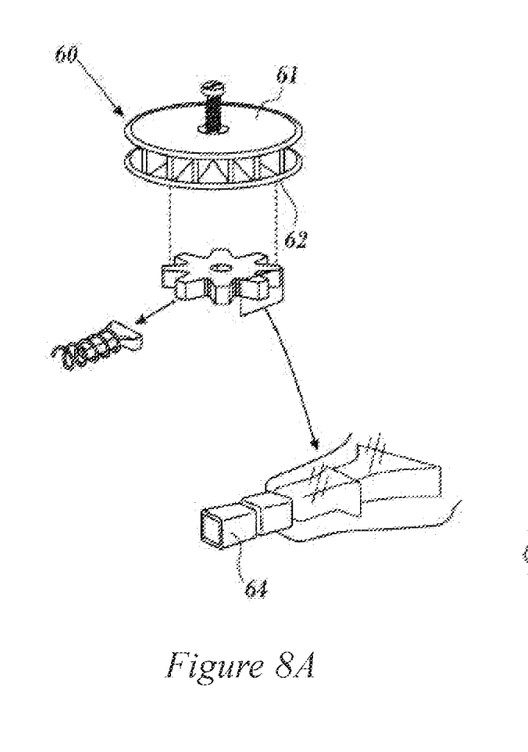
FIGS. 8 to 13 show schematic views of several alternative gyroscope assemblies.
Figures 8B, 8C, 8D:
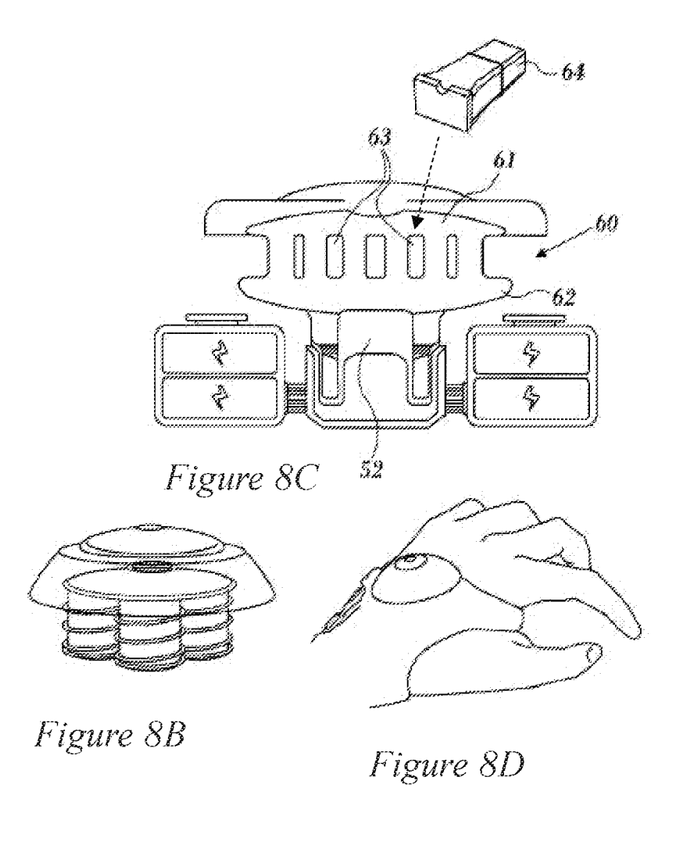

In preferred embodiments, additional stability is provided to the fingers by means of a resistive control device, for example resistive bands or dampers such as is shown in FIG. 7, in which magnetorheological fluid dampers 55 are used, disposed about the upper surface of the glove. Such elements may also be mounted about the lower and side surfaces, as required by the requirements of the patient's treatment. These resistive methods can couple the fingers to the main gyroscope housing 42 for additional control of tremor. The elements of the resistive control device can be housed within a separate layer from the gyroscopic units or as components of the gyroscopic housings.

FIGS. 8A through 8D show two variations of a modified gyroscope disc 51 in the form of a disc 60 having spaced upper and lower surfaces 61, 62 and a plurality of apertures 63 disposed circumferentially about an outer surface of the disc 60. Each aperture 63 is adapted to receive a peg 64, which adds mass to the disc, principally to a radially outward portion, thereby providing an alternative mode for adjusting the torque characteristics of the gyroscope. This method of adjusting the characteristics of a gyroscope forms a distinct and general aspect of the present invention.

Figure 9:
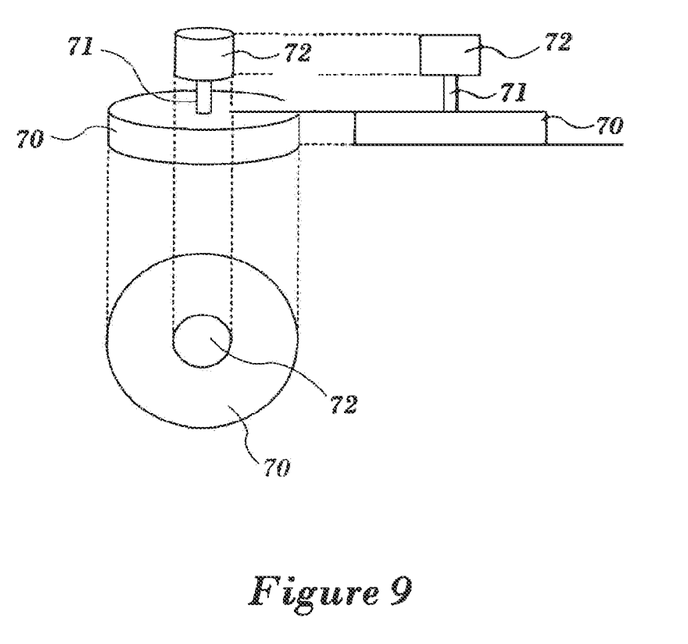
Figure 10:
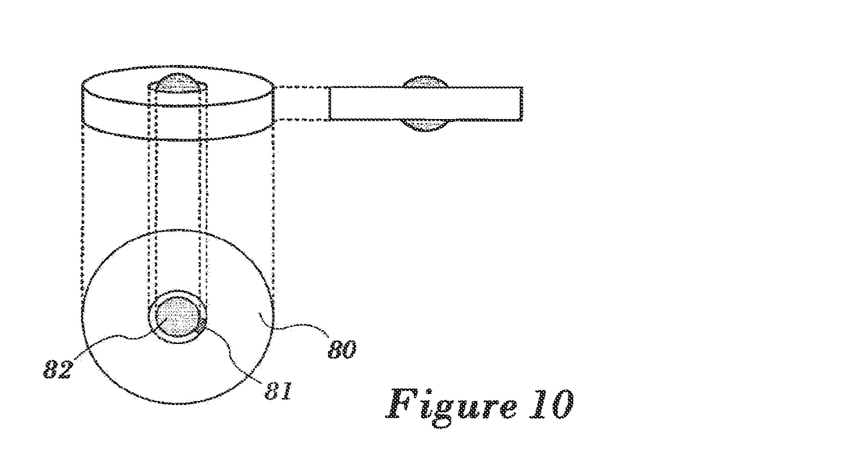

FIGS. 9 to 13 schematically show various gyroscope arrangements. The various components are represented schematically, not literally. FIG. 9 shows a conventional construction in which gyroscope disc 70 is coupled by a shaft 71 to a brushed or brushless DC motor 72. In FIG. 10, the assembly has been made more compact by mounting motor 82 within a central circular aperture formed within disc 80. Motor 82 is arranged to drive disc 80 through a transmission wheel or gear 81.

Figure 11:
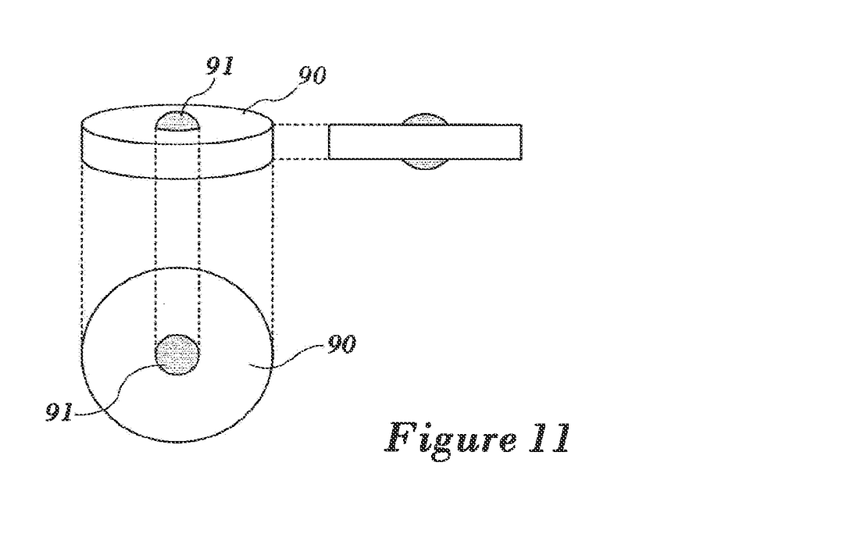
Figure 12:
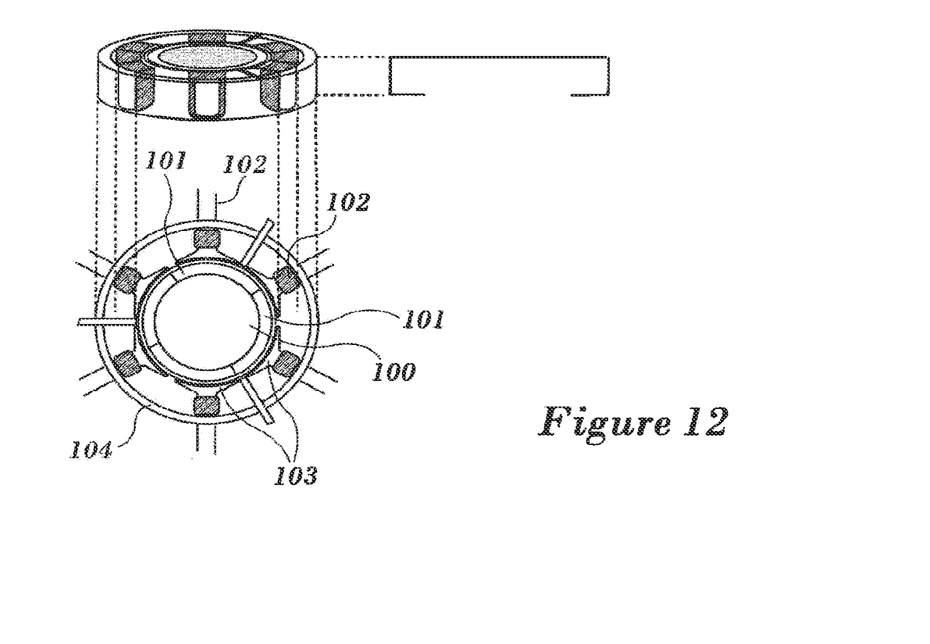
Figure 13:
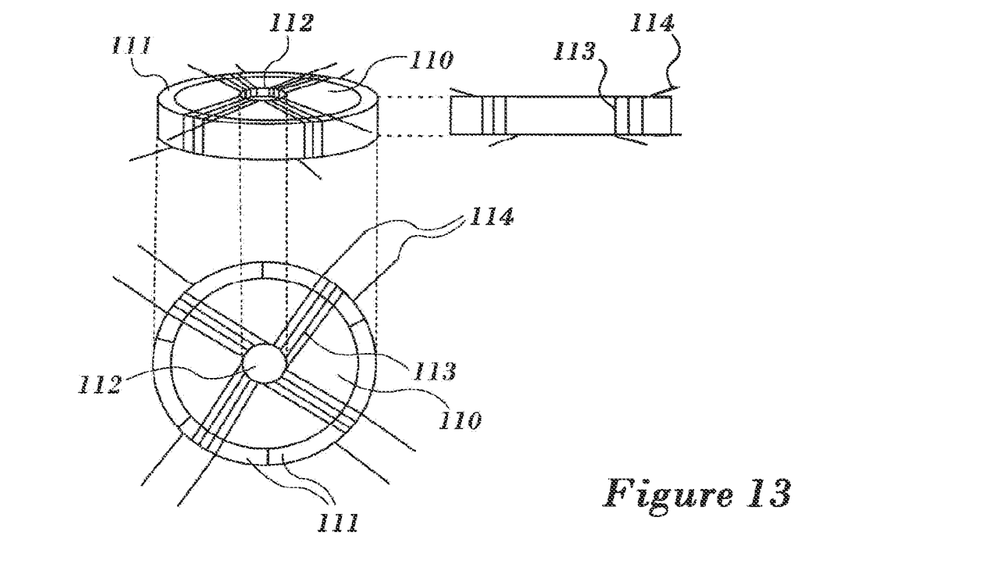

In the embodiment of FIG. 11, disc 90 is directly formed integrated with the motor 91. In the gyroscope of FIG. 12, the gyroscope itself is effectively the motor. Gyroscope disc 100 is mounted centrally within the gyroscope and has a plurality of magnets 101 of alternating polarity mounted about its outer circumference. The assembly is mounted within an annulus of alternating field windings 102 with field poles 103 mounted within a frame 104. Gyroscope disc 100 acts as the rotor of the motor and is caused to rotate by means of a correspondingly alternating polarity of the windings 102 in a conventional manner. The embodiment of FIG. 13 works as a motor in the same way as the embodiment of FIG. 12 save that disc 110 with annular alternating polarity magnets 111 has a central aperture 112 through which coil windings 113 pass, which windings are coupled by leads 114 to the electrical supply.

In certain preferred embodiments, the apparatus includes a heat management system to remove heat generated by the spinning gyroscopes. Suitably, the heat management system includes the use of heat-dispersing housings to the gyroscopes. Preferably, the housings include a heat sink arrangement to enhance heat removal. Conveniently, the wearable device, such as a glove, includes heat channelling to disperse heat to the glove, thereby allowing the glove to warm a user's hands, in use. Advantageously, a thermally reflective lining is applied between the gyroscopic devices and the wearable element to reflect heat away from the wearer's body, thereby avoiding localised heating and allowing the heat management system to provide managed warming of the body.

In preferred embodiments, the apparatus of the present invention includes additional functionality, in particular telemetries to provide feedback to a clinician on the operation of the apparatus and monitoring of other parameters of the body, such as blood pressure, pulse, temperature and skin conductivity (such as would vary with sweating et cetera). Additionally, global positioning functionality (GPS) is optionally provided, preferably along with tracking functionality such that patients with additional health concerns such as dementia can be tracked using the apparatus. In certain preferred embodiments, the apparatus incorporates one or more accelerometer devices. These will detect a sudden significant movement of the wearer, such as in the case of a fall.

Preferably, the apparatus further includes a telecommunications module, such as Wi-Fi®, Bluetooth®, GSM, GPRS, 3G, 4G and their developments).

Thereby, data from the apparatus can be communicated back to a clinician or career or, in potentially life-threatening cases such as a fall of loss of a pulse, to the emergency services or other emergency contacts. The constructional and programming details of such additional functionality will be readily apparent to the skilled person and will not be described in further detail here.

Thus, the apparatus can also be used clinically to monitor the progress of a degenerative disease such as Parkinson's Disease where tremors can vary on a daily basis; and to monitor the effectiveness in alleviation of the symptoms of the disease by medication or following surgical or other techniques. It can also be used to track the general health and wellbeing of the wearer.

Further modifications to the apparatus include the inclusion of near field communication functionality. Common social activities requiring fine motor skill, such as retrieving coins and notes for payment at a cashier are difficult for individuals with Parkinson's Disease, Essential Tremor or other musculoskeletal conditions and significant stigma or simply frustration or embarrassment can attach to these conditions. Near field communication can be built into the device and programmed by suitable computer, tablet or smartphone connectivity, for example, to allow for contactless payment and other payment systems, such as Apple Pay or Google Wallet. Further integration with other devices can be included, such as with brain pacemakers.

Remote monitoring functionality helps reduce costs of healthcare and increases convenience for users, especially non-mobile patients. With GPS functionality, the device can also act as a position tracker, to determine the location of the patient.

Although principally described with respect to stabilisation of hand tremors, the apparatus of the present invention is equally suitable for other parts of the body, including the head, legs and arms, both singly and in combination using a plurality of apparatus.

The apparatus can be used in tracking tremors, for example in physiotherapy and in training situations—surgical, sports and other applications.

The following statements summarise optional additional components of an apparatus and their advantages:
1. Social interaction functions—sounds, voice and video communications, vibration, squeezing/pressure, warmth. If a child thinks of a grandparent, or users think of each other, they either squeeze the device, associated device, smartwatch, or send a smartphone alert, which initiates pressure, warmth with possible addition of alerts, voice and video communications. Potentially helps prevent isolation, loneliness, cognitive decline et cetera.
2. Memory storage within device:
   a. Entertainment,
   b. Contacts,
   c. Emergency calls e.g. with hotkeys,
   d. Agenda, appointments, schedules, reminders.
3. Gyroscope speed sensors (phonic wheel, optical tachometers, stroboscopes) which are distinct from intelligent speed controls. Allows tracking of gyroscope speeds and subsequently ties with user adjustability. Also allows inclusion of control means to reduce power draw and increase efficiency. Intelligent speed controls both autonomously and in conjunction with manual control and user settings.
4. Smartphone apps and other user interfaces—including peripheral applications such as medicine tracking, brain pacemaker integration.
5. Speaker and microphone.
   a. Social,
      i. 2 way communication between user and permissible parties,
   b. Safety.
6. Means of alerting user, including flashing lights, vibrations, piezo electric devices.
   a. User alerts,
   b. Encourage movement for health risks,
   c. Physiotherapy, and training for other applications.
7. Physiotherapy.
8. SIM card—for telecommunications and data transfer in the event of wireless network protocol unavailability.
9. Safety features and casing functions—water-proofing, weather-sealing or high ingress protection rating, shock absorption, sound proofing.
10. Solar charging.
11. Remote server and cloud storage, transmission and sync services.
    a. Sync smart devices,
    b. Health professionals,
    c. Secure access and transmission of data.

Although the apparatus of the present invention has been described primarily with respect to therapeutic benefits for suffers of neurological conditions inducing relatively strong tremors, the present invention is equally suitable for other uses where stabilisation of hand vibrations (for example), such as those at a normal level caused simply by pulsation of blood flow would be beneficial, such as in sports (such as archery, darts or golf); fine arts, such as painting fine detail; photography or in surgery.

For the avoidance of doubt, features or aspects of the present invention which are described herein with respect to a specific embodiment are not limited to that embodiment.

The features described may be combined in any combination. Any and all such combinations are encompassed by the invention and shall not and do not constitute added subject matter.

What is claimed is:

1. An apparatus comprising:
   a gyroscope element having a gyroscope axis about which the gyroscope element rotates;
   a gyroscope mount member configured to mount the gyroscope element;
   wherein the gyroscope element is mounted to the gyroscope mount member to allow the gyroscope element to rotate about the gyroscope axis;
   a hinge; and
   a hinge plate to which the gyroscope mount member is mounted via the hinge;
      wherein the hinge plate is configured to mount to a first mount on a wearable element;
      wherein the hinge plate is configured to rotate with respect to the first mount of the wearable element so as to allow the gyroscope axis, via rotation of the hinge and the hinge plate, to precess relative to the wearable element.

2. The apparatus as claimed in claim 1, further comprising at least one of:
   i) an accelerometer;
   ii) a fall sensor,
   iii) a sleep sensor,
   iv) a body metrics sensor,
   v) a blood pressure sensor,
   vi) a pulse sensor,
   vii) a temperature sensor,
   viii) a skin conductivity sensor, and
   ix) a sweat sensor.

3. The apparatus as claimed in claim 1, further comprising:
   a battery power supply mounted to the wearable element; and
   a connector connecting the battery power supply with a motor configured to drive the gyroscope element to rotate about the gyroscope axis.

4. The apparatus as claimed in claim 3, wherein the connector is formed integrally with the wearable element.

5. The apparatus as claimed in claim 1, wherein the wearable element includes a gyroscope-receiving cup.

6. The apparatus as claimed in claim 1, further comprising a gyroscope housing for the gyroscope element.

7. The apparatus as claimed in claim 1, wherein the first mount is formed integrally with the wearable element.

8. The apparatus as claimed in claim 1, wherein the hinge plate comprises the hinge to which the gyroscope element is mounted via a connection at the gyroscope axis.

9. The apparatus as claimed in claim 1, wherein the first mount comprises a turntable to which the hinge plate is mounted so as to allow the hinge plate to rotate with respect to the wearable element.

10. The apparatus as claimed in claim 1, further comprising a control arrangement to control a precession of the gyroscope axis of the gyroscope element; and
wherein the control arrangement comprises a plurality of elastomeric dampers.

11. The apparatus as claimed in claim 1, further comprising a control arrangement to control a precession of the gyroscope axis of the gyroscope element; and
wherein the control arrangement comprises a magnetic control arrangement comprising at least one magnetic disc or annular magnet associated with the gyroscope element.

12. The apparatus as claimed in claim 1, further comprising a control arrangement to control a precession of the gyroscope axis of the gyroscope element; and
wherein the control arrangement comprises a stepped motor and gear arrangement.

13. The apparatus as claimed in claim 1, further comprising a battery power supply.

14. The apparatus as claimed in claim 1, wherein the gyroscope element is powered wirelessly and the apparatus further comprises a wireless power control circuit.

15. The apparatus as claimed in claim 1, further comprising a plurality of gyroscope elements;
wherein the plurality of gyroscope elements comprises the gyroscope element and at least one additional gyroscope element;
wherein the plurality of gyroscopes elements are distributed across at least one surface of the wearable element, and
wherein each gyroscope element of the plurality of gyroscope elements is substantially associated with a tremor axis of a patient.

16. The apparatus as claimed in claim 1, further comprising:
i) adjustment means for adjusting or modulating a current through a motor or voltage applied to the motor, the motor configured to drive the gyroscope element to rotate about the gyroscope axis;
ii) a global positioning system and tracking function;
iii) wireless networking functionality linkable to external computer-based systems;
iv) a heat-management arrangement comprising a heat-conductive casing;
vi) autonomous power generation for the gyroscope element comprising at least one of:
a) conductive fluid droplets between oscillating plates reclaiming energy from vibrations of motors;
b) flexible fluidic chambers incorporated into a palmar aspect of the wearable element with fluidic channels lined with associated electrodes running along a dorsal aspect of the wearable element;
c) piezoelectric transducers at a palmar surface to harness, in use, energy expended during gripping; and
d) sliding electrodes harnessing material shear along a wrist joint by enabling conductive fluid droplets to shear along electrodes.

17. A method comprising:
controlling, by a control circuit, a motor arrangement connected to a gyroscope element comprising a gyroscope disc to compensate for tremors;
wherein controlling the motor arrangement drives the gyroscope element to rotate about a gyroscope axis;
wherein the gyroscope axis precesses with respect to a wearable element via a gyroscope mount member;
wherein the gyroscope mount member comprises a hinge to which the gyroscope element is mounted;
wherein the hinge is mounted to a hinge plate that is configured to mount to a mount on the wearable element, wherein the hinge plate is configured to allow the gyroscope axis to precess, via rotation of the hinge and the hinge plate, with respect to the mount of the wearable element; and
wherein the hinge plate is attached to the wearable element.

18. The method as claimed in claim 17, further comprising:
receiving, by the control circuit, sensor signal from at least one sensor comprising at least one:
i) an accelerometer;
ii) a fall sensor,
iii) a sleep sensor,
iv) a body metrics sensor,
v) a blood pressure sensor,
vi) a pulse sensor,
vii) a temperature sensor,
viii) a skin conductivity sensor, and
ix) a sweat sensor; and
controlling, by the control circuit, the motor arrangement based at least in part on the sensor signal.

19. The method as claimed in claim 17, further comprising controlling, by the control circuit, the motor arrangement by controlling at least one of a voltage and a current through the motor arrangement.

20. The method as claimed in claim 17, further comprising controlling, by the control circuit, a plurality of elastomeric dampers to cause the gyroscope axis to precess with respect to the wearable element.

* * * * *

UNITED STATES PATENT AND TRADEMARK OFFICE
CERTIFICATE OF CORRECTION

| | | |
|---|---|---|
| PATENT NO. | : 12,411,009 B2 | Page 1 of 1 |
| APPLICATION NO. | : 17/388738 | |
| DATED | : September 9, 2025 | |
| INVENTOR(S) | : Joon Faii Ong et al. | |

It is certified that error appears in the above-identified patent and that said Letters Patent is hereby corrected as shown below:

On the Title Page

Related U.S. Application Data
DELETE:
"(63) Continuation of application No. 15/539,089, filed as application No. PCT/GB2015/054128 on Dec. 22, 2015, now Pat. No. 11,079,225."
And REPLACE with:
--"(63) Continuation of application No. 15/539,089, filed on June 22, 2017, now U.S. Patent No. 11,079,225, which is a 35 U.S.C. 371 National Stage of filed as application No. PCT/GB2015/054128, filed on Dec. 22, 2015, now Pat. No. 11,079,225."--

Signed and Sealed this
Thirtieth Day of December, 2025

John A. Squires
*Director of the United States Patent and Trademark Office*